US006326502B1

(12) United States Patent
Schulz et al.

(10) Patent No.: US 6,326,502 B1
(45) Date of Patent: Dec. 4, 2001

(54) METHOD FOR PRODUCING EPOXIDES THROUGH OLEFIN OXIDATION WITH AIR OR OXYGEN

(75) Inventors: Rolf Peter Schulz, Dinslaken; Uwe Dingerdissen, Seeheim-Jugenheim; Wolfgang Anton Herrmann, Freising; Gerhard Lobmaier, Gersthofen, all of (DE)

(73) Assignee: Aventis Research & Technologies GmbH & Co. KG (DE)

( * ) Notice: Subject to any disclaimer, the term of this patent is extended or adjusted under 35 U.S.C. 154(b) by 0 days.

(21) Appl. No.: 09/462,523

(22) PCT Filed: Jul. 8, 1998

(86) PCT No.: PCT/EP98/04241

§ 371 Date: Jan. 7, 2000

§ 102(e) Date: Jan. 7, 2000

(87) PCT Pub. No.: WO99/02511

PCT Pub. Date: Jan. 21, 1999

(30) Foreign Application Priority Data

Jul. 11, 1997 (DE) ............................................. 197 29 838
Jun. 24, 1998 (DE) ............................................. 198 28 011

(51) Int. Cl.$^7$ ...................... C07D 301/06; C07D 301/03
(52) U.S. Cl. ............................. 549/533; 549/532; 549/523
(58) Field of Search ................... 549/533, 532, 549/523

(56) References Cited

U.S. PATENT DOCUMENTS 3,668,227 6/1972 Mattucci et al. .
3,956,180 5/1976 Cavitt .

(List continued on next page.)

FOREIGN PATENT DOCUMENTS 2070406 9/1971 (FR) .

(List continued on next page.)

*Primary Examiner*—Deborah C. Lambkin
(74) *Attorney, Agent, or Firm*—Connolly Bove Lodge & Hutz LLP

(57) ABSTRACT

The present invention provides a process for the epoxidation of alkenes of the formula (1)

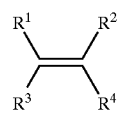

(1)

where $R^1$, $R^2$, $R^3$ and $R^4$ are, independently of one another, hydrogen, $C_1$–$C_{20}$-alkyl, $C_1$–$C_{12}$-alkoxy, $C_6$–$C_{10}$-aryl, —CHOH—CH$_3$, —CH—NH$_2$—CH$_3$ or carboxy, using air or oxygen over a catalyst comprising compounds of the formula (2)

$$Mo_xO_y(L)_z \qquad (2)$$

where
x is 1, 2 or 3,
y is an integer from 0 to 2x+1,
z is an integer from 1 to 2x,
where the ligand L is a compound of the formula (3) or (4)

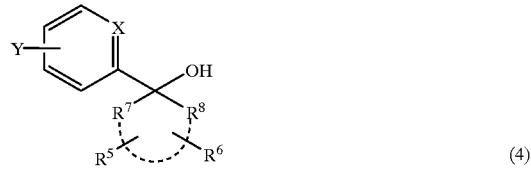

(3)

(4)

where
X is a nitrogen, oxygen or sulfur atom,
Y is hydrogen, $C_1$–$C_8$-alkyl, $C_1$–$C_8$-alkoxy, F, Cl, Br, I, COOCH$_3$, $C_6$–$C_{14}$-aryl or $C_3$–$C_8$-cycloalkyl,
$R^7$ and $R^8$ form a ring containing from 4 to 8 carbon atoms onto which one or two aromatic rings may be fused,
$R^5$ and $R^6$ are hydrogen, branched or straight-chain $C_1$–$C_{12}$-alkyl or branched or straight-chain $C_1$–$C_{12}$-haloalkyl which are substituents on the ring formed by $R^7$ and $R^8$ and/or the rings fused onto this ring,
or the ligand L is a compound of the formula (5), (6) or (7)

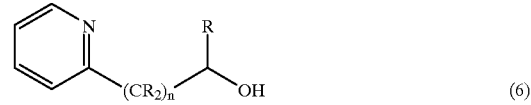

(5)

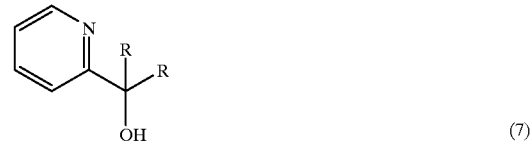

(6)

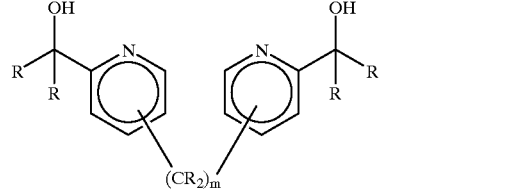

(7)

where R is hydrogen, $C_1$–$C_8$-alkyl, $C_1$–$C_8$-haloalkyl, $C_1$–$C_8$-alkoxy, COOCH$_3$, $C_6$–$C_{14}$-aryl or $C_3$–$C_8$-cycloalkyl and n is 1 or 2 and m is from 1 to 6, wherein the reaction is carried out in a pressure vessel which is completely lined with an inert material.

8 Claims, No Drawings

U.S. PATENT DOCUMENTS

| | | | |
|---|---|---|---|
| 5,817,842 | * 10/1998 | Clerici et al. | 549/531 |
| 6,031,116 | * 2/2000 | Bowman et al. | 549/523 |
| 6,063,942 | * 5/2000 | Grey | 549/523 |
| 6,229,028 | * 5/2001 | Neumann et al. | 549/523 |

FOREIGN PATENT DOCUMENTS

| | | |
|---|---|---|
| 2115752 | 7/1972 | (FR) . |
| 92/20788 | 7/1996 | (WO) . |
| 96/20788 | 7/1996 | (WO) . |

\* cited by examiner

METHOD FOR PRODUCING EPOXIDES THROUGH OLEFIN OXIDATION WITH AIR OR OXYGEN

The present invention relates to a process for preparing epoxides by catalytic oxidation of olefins using air or oxygen.

Epoxides (oxiranes), for example ethylene oxide, propylene oxide, 1,2-butene oxide or similar epoxides, are widely used intermediates in the production of a great number of products. The oxirane function in such compounds is very reactive and can undergo ring-opening reactions with nucleophilic reactants. Thus, for example, epoxides can be hydrolyzed to form glycols which are employed as deicing agents or as reactive monomers for preparing condensation polymers.

Polyether polyols prepared by ring-opening polymerization of epoxides are widely used as intermediates in the production of polyurethane foams, elastomers, coatings, sealants or similar products.

The reaction of epoxides with alcohols leads to glycol ethers which are used, for example, as polar solvents.

For the preparation of epoxides, a wide variety of processes which are supposed to selectively catalyze the epoxidation of alkenes have been developed.

Thus, for example, Huybrecht (J. Mol. Catal. 71, 129 (1992); EP-A-311 983) describes the epoxidation of olefins using hydrogen peroxide in the presence of titanium silicate compounds as catalyst. However, the range of products which is obtained in the oxidation of alkenes using titanium silicate catalysts is not sufficiently controllable, so that even minimal changes in the reaction conditions or in the reactants used lead to drastic changes in the proportions of the end products.

The epoxidation of olefins using atmospheric oxygen in the presence of tungsten- or molybdenum-containing catalysts is described in DE-C-22 35 229. The epoxidation reaction is carried out in a solvent which can be oxidized by oxygen to form hydroperoxides. However, the hydroperoxides formed lead, in further reactions, to oxygen-containing by-products, generally alcohols, which are formed as coproducts of the reaction.

A process for the epoxidation of ethylene using t-butyl hydroperoxide (TBHP) in the presence of molybdenum complexes as catalysts is described by Kelly et al. (Polyhedron, Vol. 5, 271–275, (1986)). As compounds having a high catalyst activity, mention is made of complexes such as $MoO_2$(8-hydroxyquinoline)$_2$, $MoO_2$(phenylenebissalicylimine) (=$MoO_2$(salphen)), $MoO_2$(salicylaldoxime)$_2$ and $MoO_2$(5-nitroso-8-hydroxyquinoline)$_2$. The actual active catalyst is a molybdenum complex which has undergone an addition reaction with TBHP and one equivalent of epoxide.

The process does proceed with high selectivity, but an expensive oxidizing agent is used. Furthermore, reproducibility problems occur, which prevents industrial use of the process.

The oxidation of olefins using air or oxygen as oxidizing agent would be of great advantage in industry, since the oxidizing agent is available at low cost and the reaction could proceed without formation of reduced by-products.

A process for preparing epoxides in the catalyzed liquid-phase oxidation of olefins using molecular oxygen or air is described in DD-B-159 075. Catalysts used are epoxidation-active transition metal salts or complexes of molybdenum, e.g. chloro, carbonyl or chloronitrosyl complexes which additionally contain donor ligands such as hexamethylphosphoramide (HMPA), triphenyl phosphite or acetonitrile. The most active compounds here are those which contain HMPA as donor ligands, but HMPA is known to be carcinogenic.

The epoxidation of 1-octene using molybdenum catalysts has been subject matter of a study in J. Prakt. Chem. (1992, 334, 165–175). A selectivity to 1,2-epoxyoctane of 34% is found in the presence of molybdenum acetylacetonate, and a selectivity of 28% is found in the presence of molybdenum trioxide. Likewise, it is confirmed that the position of the transition metal in the Periodic Table and its oxidation state have by far the greatest influence on the catalyst activity, while the structure of the catalyst complex itself plays only a subordinate role.

FR-A-2115752 discloses a process for the epoxidation of olefins in a titanium-lined autoclave. However, this is a non-catalytic process.

The best epoxide selectivities to date are known from DE-A-444 7231. This publication discloses molybdenum catalysts which contain an organic donor ligand. However, the catalytic activities of these catalysts are still capable of improvement.

It is an object of the present invention to provide a process which allows olefins to be oxidized highly selectively using oxygen or air to give the corresponding epoxides.

It has surprisingly been found that improved epoxide selectivities and yields are obtained using molybdenum catalysts under particular reaction conditions or when a particular procedure is employed.

The present invention provides a process for the epoxidation of alkenes of the formula (1)

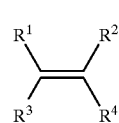
(1)

where $R^1$, $R^2$, $R^3$ and $R^4$ are, independently of one another, hydrogen, $C_1$–$C_{20}$-alkyl, $C_1$–$C_{12}$-alkoxy, $C_6$–$C_{10}$-aryl, —CHOH—$CH_3$, —CH—$NH_2$—$CH_3$ or carboxy, using air or oxygen over a catalyst comprising compounds of the formula (2)

where x is 1, 2 or 3, y is an integer from 0 to 2x+1, preferably from <1 to 2x+1, z is an integer from 1 to 2x, and 2y+z is preferably 5 or 6, where the ligand L is a compound of the formula (3) or (4)

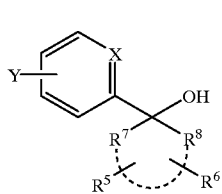
(3)

-continued

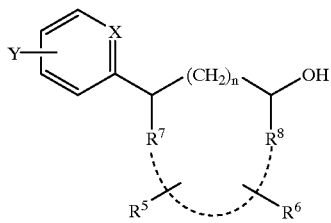
(4)

where
x is a nitrogen, oxygen or sulfur atom,
Y is hydrogen, $C_1$–$C_8$-alkyl, $C_1$–$C_8$-alkoxy, F, Cl, Br, I, $COOCH_3$,
$C_6$–$C_{14}$-aryl or $C_3$–$C_8$-cycloalkyl,
$R^7$ and $R^8$ form a ring containing from 4 to 8 carbon atoms onto which one or two aromatic rings may be fused,
$R^5$ and $R^6$ are hydrogen, branched or straight-chain $C_1$–$C_{12}$-alkyl or branched or straight-chain $C_1$–C12-haloalkyl which are substituents on the ring formed by $R^7$ and $R^8$ and/or the rings fused onto this ring,
or the ligand L is a compound of the formula (5), (6) or (7)

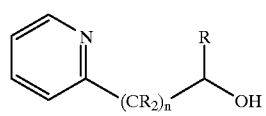
(5)

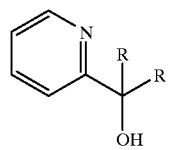
(6)

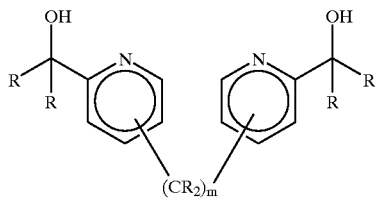
(7)

where R is hydrogen, $C_1$–$C_8$-alkyl, $C_1$–$C_8$-haloalkyl, $C_1$–$C_8$-alkoxy, $COOCH_3$, $C_6$–$C_{14}$-aryl or $C_3$–$C_8$-cycloalkyl and n is 1 or 2 and m is from 1 to 6, wherein the reaction is carried out in a pressure vessel which is completely lined with an inert material.

The ligand is generally bound in a bidentate manner to the metal center which can bind up to two such ligands. In the case of the tetradentate ligand (7), only one ligand is bound. Both cis and trans isomers of the dioxo complexes are possible.

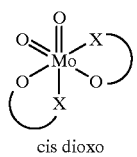
cis dioxo

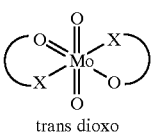
trans dioxo

Examples of preferred ligands L are the following compounds:

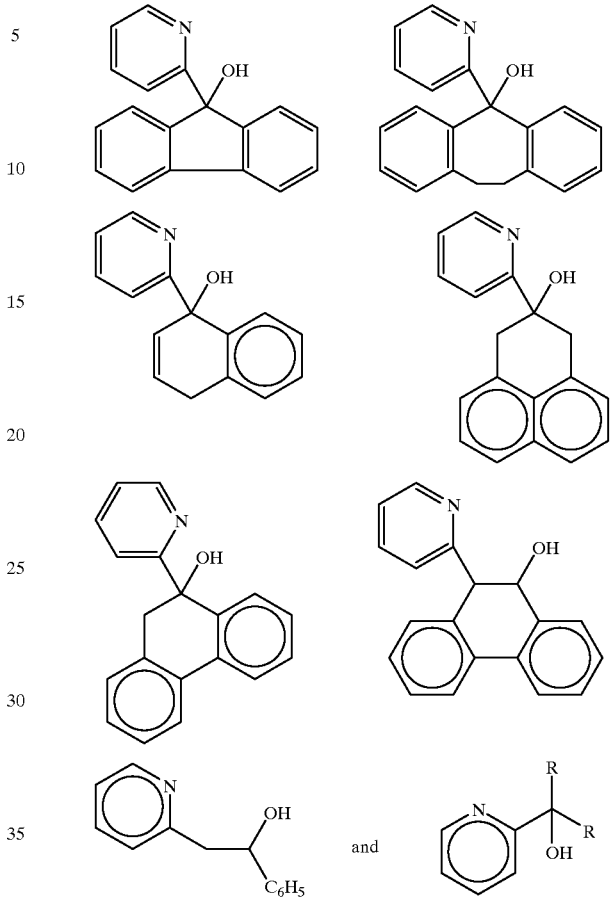

where R=$CH_3$, $C_2H_5$, i-$C_3H_7$, n-$C_3H_7$ and n-$C_4H_9$.

Complexes of the formula (2) are prepared by reacting a suitable precursor with the appropriate ligands in an organic solvent. Suitable precursors are, for example, the commercially available oxo-acetylacetonates such as molybdenyl acetylacetonate $MoO_2(acac)_2$ or oxo-dithiocarbamates, e.g. molybdenyl bis(N,N-diethyldithiocarbamate), the pyridyl and/or acetate complexes of the oxides, the higher oxides, e.g. molybdenum trioxide, or the corresponding acids and their salts.

The precursor is suspended in an organic solvent. The most suitable organic solvents are polar protic solvents such as methanol or ethanol and protic solvents such as acetonitrile or methyl tert-butyl ether (MTBE) or halogenated hydrocarbons such as $CH_2Cl_2$, $CHCl_3$ or $CCl_4$. The appropriate ligand is subsequently added while stirring. The amount of ligand used is preferably twice that of the precursor used.

After the reaction is complete, the mixture is filtered off and the residue is washed. The filtration residue obtained can be used as catalyst in this form or after drying under reduced pressure.

Supported complexes can be prepared by adding a suitable carrier material during and/or after the synthesis of the complex. For this purpose, the starting complex of the formula (2) is dissolved in an organic solvent or water, the carrier material is added and the mixture is stirred. The ratio of complex/carrier material is preferably in the range from 1:1 to 1:1000, in particular in the range from 1:2 to 1:100.

Suitable carrier materials are inorganic and organic carriers. Examples of inorganic carriers are aluminum oxides, silicon dioxides, aluminosilicates, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, silicon nitride, carbon and silicon carbide.

Suitable organic carriers are all polymers possessing donor centers which can interact with the Mo center, or functionalized polymers which form a chemical bond on reaction with the complexes of the formula (2) or ligands of the formulae (3)–(5). In the latter case, the heterogenized ligand obtained in this way has to be converted into the complex by reaction with a suitable precursor (e.g. $MoO_2$ $(acac)_2$) in an organic solvent. Examples of such carriers are polypyridines, polyacrylates and polymers containing $PR_2$, $O=PR_3$ or $NR_2$ (R=H, alkyl, aryl) groups.

In the process of the invention, the pressure apparatus necessary because of the reaction pressures required is completely lined with an inert material or has been completely freed of oxide layers. Examples of inert materials which are suitable for the lining are gold, polyethylene, titanium, glass, enamel, polytetrafluoroethene (PTFE), poly(trifluorochloroethene) (PCTFE), polyvinylidene fluoride (PVDF) and polyvinyl fluoride (PVF); preference is given to complete lining/coating of all internal surfaces of the pressure reactor with fluorine-containing polymers. To remove oxide layers, the material can be pretreated chemically or mechanically (e.g. sand blasting). The oxidizing agent employed is oxygen which can be in pure form or diluted with an inert gas such as $CO_2$, $N_2$, noble gases or methane. In a preferred continuous procedure, use is made of air, and, if desired, oxygen which has been consumed is replaced by further introduction of pure oxygen or of oxygen-containing gas mixtures.

Liquid-phase oxidations are carried out, both in the case of heterogeneous catalysts and in the case of homogeneous catalysts, either in the pure olefin or diluted in an oxidation-stable solvent. Suitable solvents are, for example, the following classes of compounds: halogenated aromatics such as chlorobenzene, 1-chloro-4-bromobenzene or bromobenzene, halogenated and unhalogenated hydrocarbons such as chloroform, chloropropanol, dichloromethane, 1,2-dichloroethane or trichloroethylene, ketones and water. The oxidation can be carried out continuously or batchwise. The catalyst can be added as such but can also be generated in situ during the catalysis, e.g. from precursor and ligand and, when using a heterogeneous catalyst, the appropriate carrier material. Furthermore, the reaction can be accelerated by addition of stoichiometric amounts, based on the catalyst, of an activator such as a hydroperoxide, hydrogen peroxide or a peracid and/or by addition of a free radical initiator such as azobisisobutyronitrile.

The oxidation conditions are selected so that appreciable oxidation occurs even without addition of catalyst, although in this case the selectivity of epoxide formation is low.

When carrying out the process continuously, the oxygen is metered in at a rate which results in a residence time in the reactor of less than 60 minutes, preferably less than 20 minutes. In a batch process, oxygen uptake can occur to complete conversion of the alkene, but preference is given to oxygen uptake to an alkene conversion of <50%, in particular <30%. The reaction product is worked up and purified, for example by distillation. This also applies to the continuous procedure, for example in bubble column reactors. The reaction is preferably carried out so that high oxygen conversions are achieved. This can be achieved, for example, by setting high propene/oxygen ratios and introducing further oxygen into the system to replace that which has been consumed.

The temperature at which the epoxidation reaction can be carried out is in the range from 80 to 300° C.; the pressure can be from atmospheric pressure to 200 bar and is preferably not above 100 bar. Thus, for example, a pressure range of from 80 to 250° C. and a pressure in the range from atmospheric pressure to 30 bar has been found to be advantageous in the oxidation of $C_6$–$C_{12}$-alkenes, while the epoxidation of alkenes having less than 6 carbon atoms is preferably carried out at temperatures in the range from 120 to 300° C. and pressures in the range from 30 to 100 bar.

The epoxidation of octene using the catalysts set forth in the present invention is generally carried out in a temperature range from 80 to 300° C., preferably in the range from 80 to 130° C. and a pressure of from 1 to 30 bar. In the case of propene, the temperature is preferably in a range from 100 to 300° C., in particular in the range from 125 to 230° C., particularly preferably from 135 to 200° C. The pressure should be in the range from 30 to 150 bar, in particular from 35 to 100 bar. The process of the invention is therefore notable not only for the use of inert reactor materials but also for the fact that the reaction is carried out under comparatively mild reaction conditions and that high epoxide yields are achieved in this way.

EXAMPLES

Influence of the Reactor Wall Material

Types of autoclave used:

A Hastelloy autoclave (without insert)

B Hastelloy autoclave with PTFE insert; autoclave lid made of Hastelloy without PTFE lining C autoclave lined completely with PTFE Reaction conditions: 20 ml of chlorobenzene, 150° C., 25–27 g of propene

TABLE 1

| Catalyst | Amount of cat. mg | J min | PO selectivity % | P (air) bar | Autoclave type |
|---|---|---|---|---|---|
| $MoO_2(ethyl)_2$ | 20 mg | 6 | 17 | 16 | A |
| $MoO_2(ethyl)_2$ | 2 mg | 6 | 27 | 15 | A |
| $MoO_2(methyl)_2$ | 2 mg | 10 | 26 | 15 | A |
| $MoO_2(methyl)_2$ | 5 mg | 10 | 42 | 30 | B |
| $MoO_2(ethyl)_2$ | 5 mg | 15 | 45 | 15 | B |
| $MoO_2(ethyl)_2$ | 5 mg | 15 | 48 | 31 | B |
| $MoO_2(ethyl)_2$ | 28 mg | 12 | 66 | 10 | C |
| $MoO_2(methyl)_2$ | 28 mg | 12 | 71 | 10 | C |

Influence of the Temperature

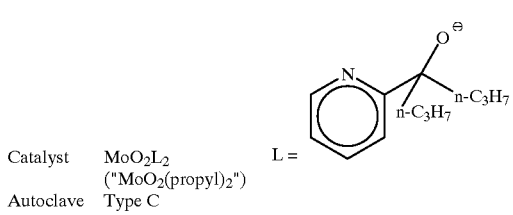

| Catalyst | $MoO_2L_2$ ("$MoO_2(propyl)_2$") | L = |
| Autoclave | Type C | |

TABLE 2

| Reaction temperature T [° C.] | Reaction time J [min] | Propene conversion % | $O_2$ conversion % | PO selectivity % |
|---|---|---|---|---|
| 130 | 12 | — | — | — |
| 140 | 12 | 2.4 | 40 | 71 |
| 145 | 12 | 1.8 | 32 | 72 |
| 150 | 12 | 5.4 | 87 | 72 |

Influence of Pressure and Reaction Time

Catalyst  $MoO_2L_2$ ("MoO$_2$(propyl)$_2$") L = 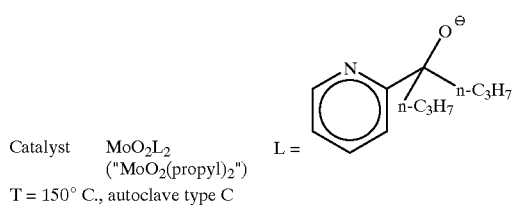

T = 150° C., autoclave type C

TABLE 3

| Reaction time [min] | Reaction pressure [bar] | Propene conversion % | PO selectivity % |
|---|---|---|---|
| 9 | 46 | 5.8 | 71 |
| 24 | 33 | 5.6 | 63 |
| 12 | 33 | — | — |
| 64 | 18 | 5.8 | 63 |
| 12 | 16 | — | — |
| 9 | 42 [145° C.] | 1.8 | 72 |
| 12 | 42 [145° C.] | 0.2 | — |

What is claimed is:

1. A process for the epoxidation of alkenes of the formula (1)

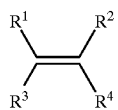

(1)

where $R^1$, $R^2$, $R^3$ and $R^4$ are, independently of one another, hydrogen, $C_1$–$C_{20}$-alkyl, $C_1$–$C_{12}$-alkoxy, $C_6$–$C_{10}$-aryl, —CHOH—CH$_3$, —CH—NH$_2$—CH$_3$ or carboxy, using air or oxygen over a catalyst comprising compounds of the formula (2)

$$Mo_xO_y(L)_z \quad (2)$$

where $x$ is 1, 2 or 3, $y$ is an integer from 0 to 2x+1, $z$ is an integer from 1 to 2x, where the ligand L is a compound of the formula (3) or (4)

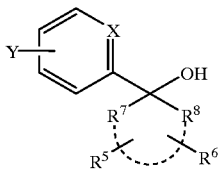

(3)

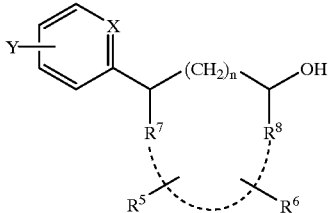

(4)

where

X is a nitrogen, oxygen or sulfur atom,

Y is hydrogen, $C_1$–$C_8$-alkyl, $C_1$–$C_8$-alkoxy, F, Cl, Br, I, COOCH$_3$, $C_6$–$C_{14}$-aryl or $C_3$–$C_8$-cycloalkyl, $R^7$ and $R^8$ form a ring containing from 4 to 8 carbon atoms onto which one or two aromatic rings may be fused, $R^5$ and $R^6$ are hydrogen, branched or straight-chain $C_1$–$C_{12}$-alkyl or branched or straight-chain $C_1$–$C_{12}$-haloalkyl which are substituents on the ring formed by $R^7$ and $R^8$ and/or the rings fused onto this ring, or the ligand L is a compound of the formula (5), (6) or (7)

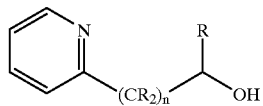

(5)

(6)

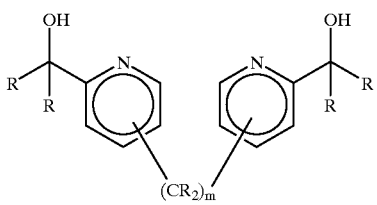

(7)

where R is hydrogen, $C_1$–$C_8$-alkyl, $C_1$–$C_8$-haloalkyl, $C_1$–$C_8$-alkoxy, COOCH$_3$, $C_6$–$C_{14}$-aryl or $C_3$–$C_8$-cycloalkyl and n is 1 or 2 and m is from 1 to 6, wherein the reaction is carried out in a pressure vessel which is completely lined with an inert material.

2. The process as claimed in claim 1, wherein the ligand L is one of the following compounds:

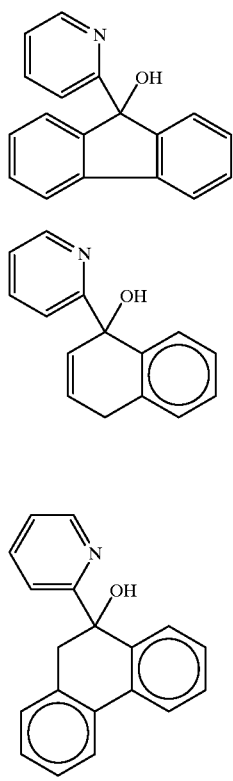
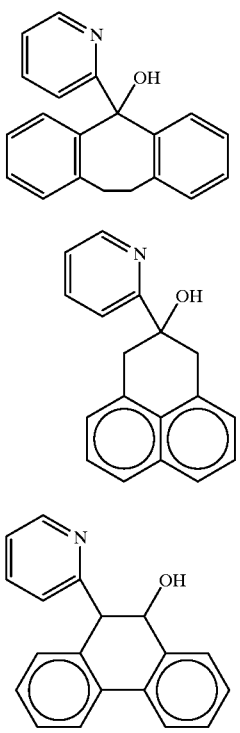
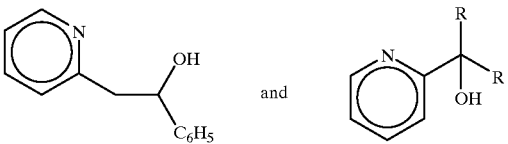

-continued where R=CH₃, C₂H₅, i-C₃H₇, n-C₃H₇ and n-C₄H₉.

3. The process as claimed in claim 1, wherein the complex has been applied to a carrier material, wherein the ratio of complex/carrier material is in the range from 1:1 to 1:1000.

4. The process as claimed in claim 3, wherein the carrier material is selected from the group consisting of aluminum oxides, silicon dioxides, aluminosilicates, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, silicon nitride, carbon and silicon carbide, polypyridines, polyacrylates and polymers containing PR₂, O=PR₃ or NR₂ (R=H, alkyl, aryl) groups.

5. The process as claimed in claim 1, wherein the reaction vessel is lined with gold, polyethylene, titanium, glass, enamel, polytetrafluoroethene (PTFE), poly (trifluorochloroethene) (PCTFE), polyvinylidene fluoride (PVDF) or polyvinyl fluoride (PVF) or has been made inert.

6. The process as claimed in claim 2, wherein said ligand is applied to a carrier material, wherein the ratio of complex/carrier material is in the range from 1:2 to 1:100.

7. The process as claimed in claim 1, wherein y≧1 and 2y+z is 5 or 6.

8. The process as claimed in claim 1, wherein the reaction is carried out at a temperature range from 80 to 300° C.

* * * * *